(12) United States Patent
Benfatti

(10) Patent No.: US 8,015,728 B2
(45) Date of Patent: Sep. 13, 2011

(54) SHOE INSERT FOR HEATING AND COOLING FOOT

(76) Inventor: Eugene L Benfatti, Roseland, NJ (US)

( * ) Notice: Subject to any disclaimer, the term of this patent is extended or adjusted under 35 U.S.C. 154(b) by 952 days.

(21) Appl. No.: 11/779,307

(22) Filed: Jul. 18, 2007

(65) Prior Publication Data
US 2007/0256324 A1    Nov. 8, 2007

Related U.S. Application Data
(60) Provisional application No. 60/852,071, filed on Oct. 16, 2006.

(51) Int. Cl.
*A43B 7/02* (2006.01)
*A43B 13/38* (2006.01)
(52) U.S. Cl. .............. 36/2.6; 36/43; 36/44; 36/153
(58) Field of Classification Search ............. 36/2.6, 36/97, 3 R, 29, 43, 44, 71, 154, 153
See application file for complete search history.

(56) References Cited

U.S. PATENT DOCUMENTS

| | | |
|---|---|---|
| 752,516 A | 2/1904 | Carney |
| 2,680,918 A | 6/1954 | Behner |
| 3,493,986 A | 2/1970 | Erwin |
| 3,585,736 A | 6/1971 | Polichena |
| 3,946,193 A | 3/1976 | Giese |
| 4,023,282 A | 5/1977 | Ziegelheafer |
| 4,094,080 A | 6/1978 | Sanders |
| 4,249,319 A | 2/1981 | Yoshida |
| 4,331,731 A * | 5/1982 | Seike et al. ............. 428/305.5 |
| 4,387,516 A * | 6/1983 | Laux ....................... 36/43 |
| 5,084,986 A | 2/1992 | Usui |
| 5,167,999 A * | 12/1992 | Wang ...................... 428/178 |
| 5,230,170 A * | 7/1993 | Dahle ...................... 36/2.6 |
| 5,375,430 A | 12/1994 | Siegel |
| 5,591,221 A | 1/1997 | Owens |
| 5,606,806 A | 3/1997 | O'Dwyer |
| 6,085,444 A | 7/2000 | Cho |
| 6,098,315 A * | 8/2000 | Hoffmann, III ........... 36/91 |
| 6,301,805 B1 * | 10/2001 | Howlett et al. ............ 36/43 |
| 6,328,761 B1 * | 12/2001 | Ueki ....................... 607/111 |
| 6,594,917 B2 | 7/2003 | Ricco et al. |
| 6,631,568 B2 * | 10/2003 | Howlett et al. ............ 36/43 |

(Continued)

*Primary Examiner* — Marie Patterson
(74) *Attorney, Agent, or Firm* — Stanley H. Kremen

(57) ABSTRACT

A shoe insert to be used for heating or cooling the foot. They are to be manufactured and sold as pairs of left and right shoe inserts. The insert has a number of components forming a sandwich within a sandwich. The outer sandwich has the shape of a shoe, and is partly adjustable in size to fit a range of shoe sizes. So, the inserts may be sold in sizes, for example, small, medium, and large, and these sizes may then be fine tuned to fit a sub-range of shoe sizes. The inner sandwich is smaller than the outer sandwich. The inner sandwich is a pouch positioned at the instep which ruptures when pressure is applied. This pouch contains a liquid that can then flow into a cushioned region. The cushioned region contains a chemical, which when combined with the liquid from the pouch, emits heat (exothermic reaction) or absorbs heat (endothermic reaction). An exothermic reaction would heat the foot while an endothermic reaction would cool the foot. The bottom component of the cushioned layer has round dimples into which a dry chemical can be placed. Alternatively the cushioned layer can have a liquid different from that in the pouch. Heating can be accomplished, for example, by precipitating a supersaturated solution of sodium acetate in water. Cooling can be accomplished, for example, by combining ammonium nitrate with water.

11 Claims, 3 Drawing Sheets

U.S. PATENT DOCUMENTS

| | | |
|---|---|---|
| 6,865,825 B2 | 3/2005 | Bailey, Sr. et al. |
| 6,893,453 B2 | 5/2005 | Agarwal et al. |
| 6,959,505 B2 * | 11/2005 | Poe .................................. 36/43 |
| 7,017,283 B2 | 3/2006 | Shows |
| 7,124,520 B2 * | 10/2006 | Galbraith et al. ................. 36/43 |
| 2006/0230633 A1 * | 10/2006 | Polenta ............................ 36/2.6 |

* cited by examiner

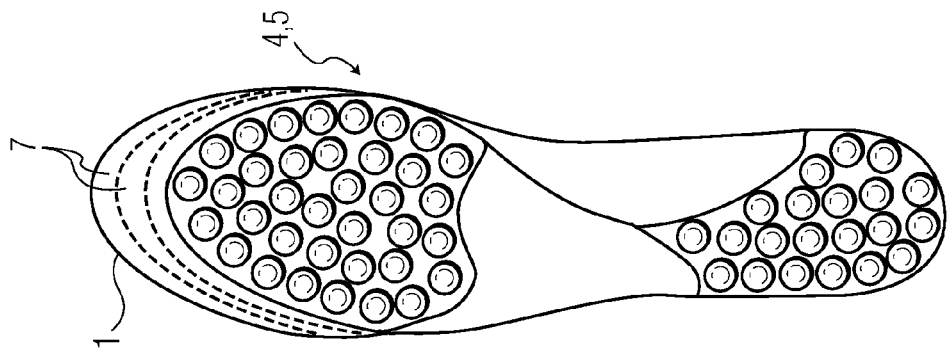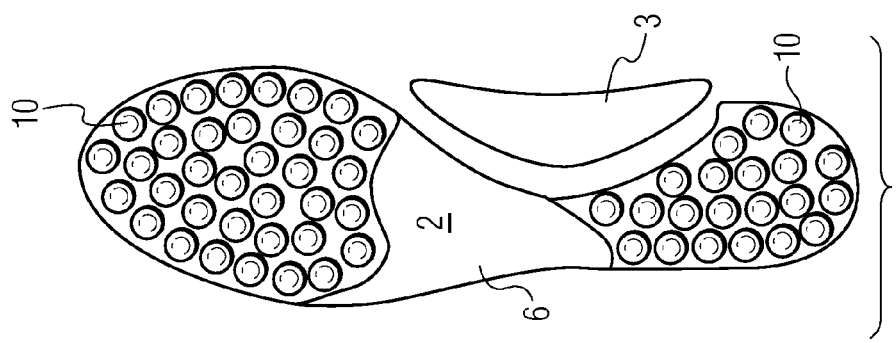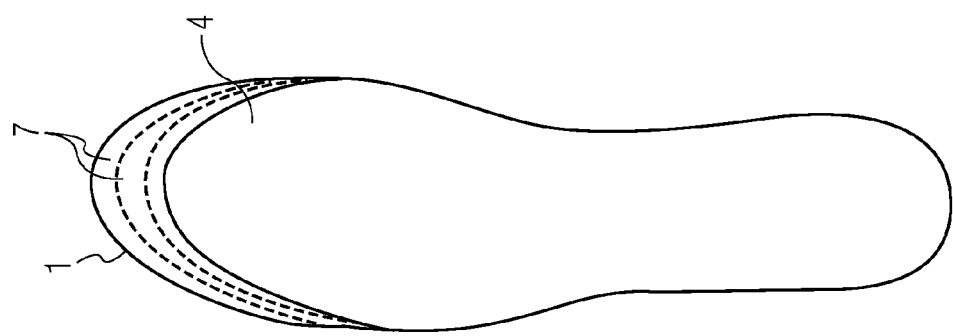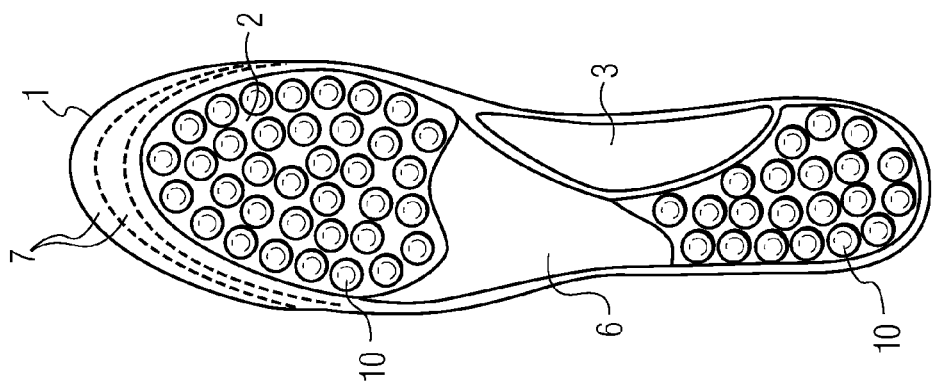

SHOE INSERT FOR HEATING AND COOLING FOOT

CROSS REFERENCE TO RELATED APPLICATIONS

This Present Application is the non-provisional counterpart of and claims the benefit of and priority to U.S. Provisional Application Ser. No. 60/852,071 filed on Oct. 16, 2006 which is incorporated by reference herein in its entirety.

BACKGROUND OF THE INVENTION

Insoles and inserts for shoes have long been popular to increase the comfort level of the shoe wearer. They are primarily designed to cushion or provide additional support for the foot for both medical and non-medical reasons. A fairly recent innovation in shoe inserts is the use of liquid or gel-filled cavities within the insert to provide an adaptive, form-fitting cushion and a more even distribution of force onto the sole of the foot.

This typically involves having a pouch of the liquid or gel within the insert which allows the substance inside to move freely about inside the insert, thus conforming to the shape of the foot. Problems arise with this type of insert construction as it is possible for all the liquid or gel to pool in a single location, thereby negating the benefits of the force-distributive properties of the liquid or gel.

Another innovation to come to footwear is that of temperature control within the shoe. Most common is the use of heat production in a shoe insert. Though there are some employing electrical means of heat production, the most common form is the use of exothermic chemical reactions which provide a steady, relatively long-duration source of heat.

The second, less common form of temperature control within the shoe is by means of decreasing the temperature. Like heated inserts, there are examples that use electrically powered means of cooling the shoe, but there is no prior art employing an endothermic chemical reaction to serve this purpose.

The electrically powered means of temperature in both cases are impractical for everyday use as the effort required to maintain the desired temperature with such devices exceeds the perceived benefit of the devices, hence their failure to gain a position within the shoe insole market.

SUMMARY OF THE INVENTION

The Present Invention overcomes the drawbacks perceived in the prior art, both of the problems arising from uneven distribution of liquids or gels within pouches in the shoe inserts and the lack of a chemical means of controlling the temperature of the shoe interior. The present invention is an insole comprising a plurality of wells within the sealed interior of the insole which maintains an even dispersal of a chemical solution responsible for providing or reducing heat.

BRIEF DESCRIPTION OF THE DRAWINGS

FIG. 1 shows the left shoe insert.
FIG. 1(a) is a top plan view of the entire shoe insert.
FIG. 1(b) is a top plan view of the lower layer of the shoe insert. A pouch containing one of the chemical components is shown alongside and to the right of the lower layer.
FIG. 1(c) is a top plan view of the cushioned layer component of the insert.
FIG. 1(d) is a top plan view of the upper layer of the insert.
FIG. 2 shows the pouch.
FIG. 3 shows the cushioned layer without the pouch.

DETAILED DESCRIPTION OF THE INVENTION

Figure 2A:
FIG. 2(a) is a side elevation view of the pouch.

This invention, in its preferred embodiment, comprises two layers of a thin, durable material such as vinyl heat sealed along the perimeter of the material roughly in a shape matching the outline of the average foot, though those skilled in the art would also perceive of the benefit of producing a roughly oval shape. The lower layer is of greater thickness than that of the top layer, such that indentions of approximately $1/8$ inch may be placed in the lower level without weakening the integrity of the pouch. Between the upper and lower levels reside spherical granules of Ammonium Nitrate evenly distributed throughout most of the volume and a cellophane pouch filled with an appropriate volume of water so as to completely saturate the Ammonium Nitrate granules once the pouch is ruptured.

Those skilled in the art may be able to perceive of additional embodiments such as different endothermic chemical reactions or altering the size of the indentations within the bottom layer of the pouch and adjusting the size of the granules to fit accordingly into said indentations.

The user of the preferred embodiment of present invention would burst the cellophane pouch of water within the shoe insert and gently agitate the mixture inside until the Ammonium Nitrate has been fully inundated with the water. The user then places the insert within his shoe and proceeds to put on his shoe as usual. Within the shoe, the application of force from the foot does not displace all of the fluid from the areas receiving the most force due to the indentations in the bottom layer of the insert. The cooling liquid is pooled within the indentations, is thus kept from flowing away from the foot to the sides. This allows for even distribution of the cooling liquid, thereby maximizing the cooling effect of the insert.

An additional embodiment of the present invention creates an increase in temperature within the insert. Using the same pouch design of having two sheets of vinyl heat sealed with the bottom layer having small indentations, the pouch is instead filled with a volume of supersaturated Sodium Acetate and a trigger to activate the supersaturated salt solution, such as the one described in U.S. Pat. No. 4,572,158. When the trigger is deformed by manually bending it within the sealed pouch, it creates a seed crystal which causes the supersaturated solution to precipitate out, releasing a large amount of heat over several hours' time. Of interest in this particular chemical reaction and catalyst combination is the fact that it is reversible, which makes the insole reusable. Continued application of heat will cause the Sodium Acetate precipitate to go back into a supersaturated liquid form, thus allowing the insert to be used again.

FIG. 1(a) is a top plan view of the entire shoe insert assembly for the left foot. The right foot shoe insert is identical to the left foot shoe insert shown in FIG. 1, but is the left-right reversed mirror image. The right foot shoe insert is not shown in the drawings. The toe end of the insert on the top layer 1 extends beyond the cushioned region 2. Alternatively, the extension of the toe end may be on both layers 1 and 2. Shown is the pouch 3 which contains one of the chemical components necessary to produce heating or cooling. For example, in the cooling case, the main section of the cushioned insert could contain a measured amount of ammonium nitrate spheres, while the pouch could contain a combination of water and glycerin. Even though it is shown separated from the cushioned layer, it is actually an integral part of the cushioned layer.

FIG. 1(b), FIG. 1(c), and FIG. 1(d) represent top plan views of the various shoe insert components. FIG. 1(b) shows the top layer 4. At the toe end are break-away strips 7 to adjust the insert to the shoe size. Therefore, the insert may be manufactured either in a single size or in a few sizes such as small, medium, and large. By breaking away the strips 7, the wearer is able to place the insert into a shoe of any size. Clearly, the break-away strips adjust the size of both the top layer 1 (shown in FIG. 1(d)) as well as bottom layer 4. The cushioned insert 2 is smaller than top layer 1 and bottom layer 4. In the preferred embodiment, top layer 1 and bottom layer 4 are equal in size and dimensions. They are attached at their perimeters, preferably by a welded seam, so as to seal in the cushioned layer and the pouch 3. Breaking off the break-away strips 7 to adjust the size of the insert does not expose the cushioned region 2 since the perimeter attachment of the top and bottom layers is placed where the insert size is smallest. Beyond that position and extending to the end of the toe, the top and bottom layers adhere to each other. The break-away lines are formed so as ease the process of breaking or tearing excess material away from the toe end of the insert. The process of breaking away the strips does not damage the rest of the insert. FIG. 1(c) is a top plan view of bottom layer 5 of cushioned region 2, and FIG. 1(d) is a top plan view of the top layer 1. Shown in FIG. 1(c) along side of the bottom layer is the pouch.

Figure 2B:
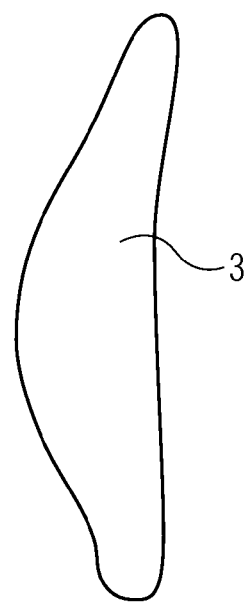
FIG. 2(b) is a top plan view of the pouch.

FIG. 2(a) represents a side elevation view of the pouch 3, while FIG. 2(b) represents a top plan view of the pouch alone. The pouch is an integral part of the cushioned insert, and is attached to the instep portion of the cushioned insert. The pouch contains liquid, and is designed to rupture from pressure applied to the pouch. The pouch ruptures on the left-most end of its perimeter so as to release liquid into the cushioned region. With a right shoe insert, the pouch is the left-right reversed mirror image of the one shown in FIGS. 1 and 2. A right shoe insert pouch ruptures on the right-most end of its perimeter so as to release liquid into the cushioned region.

Figure 3A:
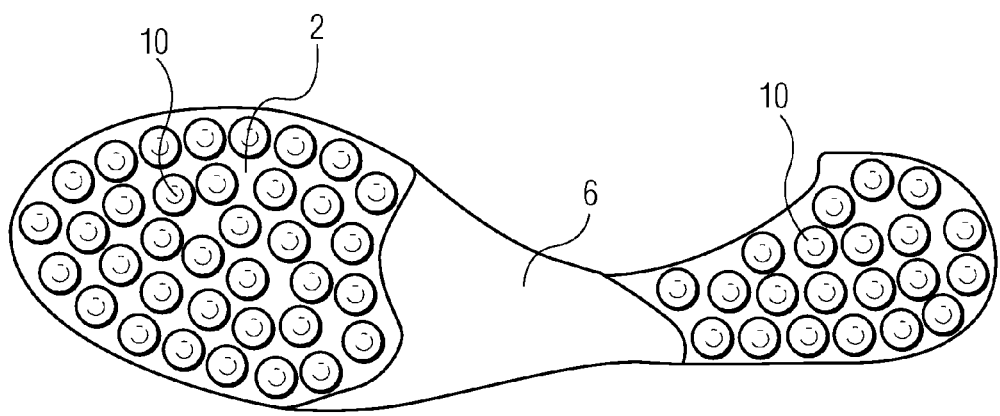
FIG. 3(a) is a top plan view of the cushioned layer.
Figure 3B:
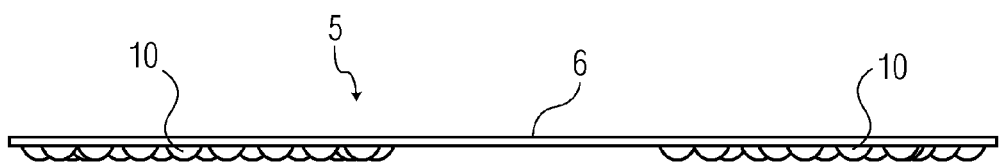
FIG. 3(b) is a side elevation view of the bottom component of the cushioned layer.

FIG. 3 shows the cushioned region 2. This region is sandwiched between the top layer 1 and the bottom layer 4. The pouch, which is part of the cushioned region, is not shown. The cushioned region itself comprises three parts:
 a top component;
 a bottom component; and,
 a pouch.
The three parts are attached inseparably, preferably with a welded seam. FIG. 3(a) is a top plan view of the cushioned region. In its preferred embodiment, the material used in fabrication of the entire shoe insert is clear (transparent) PVC Vinyl (~0.3 mm). Therefore, the top plan view of the entire insert provides visibility of the entire structure. As previously discussed, the pouch contains a liquid that, when the pouch ruptures, flows into the region (volume) between the top component and the bottom component. The perimeter region of the pouch that ruptures is the same as the corresponding instep perimeter of the top-bottom component sandwich. It is a single boundary between the pouch and the sandwich. The top component 1 is uniform. However, the bottom component 4 comprises round (preferably circular) dimples 10 that are depressions in the material. The dimples may be formed by heat pressing into the bottom component 4. The region between the sandwich may contain a liquid other than that in the pouch or may be dry (not contain any liquid). In the case of a shoe insert designed to cool the foot, measured amounts of ammonium nitrate (for example) are placed into each of the dimples and water (possibly mixed with a viscous liquid) is placed into the pouch. When the pouch ruptures, the water flows into the sandwich and makes contact with the ammonium nitrate. The resulting chemical reaction is endothermic, and the shoe insert becomes cold. In the embodiment shown in FIG. 3, the bottom component comprises three separate regions—i.e., two dimpled regions 10 separated by a non-dimpled region 6.

Persons having ordinary skill in the art will be able to see that variations in the geometry are obvious and that different chemicals and materials may be inserted into the pouch and cushion sandwich such that when combined, produce either an exothermic chemical reaction for heating the foot or an endothermic reaction for cooling the foot.

I claim:

1. A shoe insert shaped like a shoe insole and having a heel end, a toe end, and an instep, said insert having a cushioned layer comprising:
 a) a flexible and supple upper component;
 b) a lower component; and
 c) a pouch that contains liquid,
 wherein:
 the upper and lower components are attached and sealed inseparably to each other at their respective perimeters, said attachment forming a volume;
 the lower component comprises a plurality of indentations;
 the pouch is positioned at the instep and shares a sealed common boundary with the upper and lower components;
 the pouch contains a liquid;
 the volume between the upper and lower components contains a chemical substance;
 the common boundary between the pouch and the upper and lower components separates the liquid contents of the pouch and the volume formed between the upper and lower components; and,
 the common boundary between the pouch and the upper and lower components is weaker than the rest of the seal between the upper and lower components, such that when sufficient pressure is applied to the pouch, the common boundary ruptures, thereby permitting the liquid from the pouch to enter into the volume between the upper and lower components and to react with the chemical substance therein.

2. The shoe insert of claim 1 wherein the lower component is flexible and supple.

3. The shoe insert of claim 1 wherein the reaction between the liquid and the chemical substance is exothermic.

4. The shoe insert of claim 3 wherein the chemical substance is sodium acetate.

5. The shoe insert of claim 1 wherein the reaction between the liquid and the chemical substance is endothermic.

6. The shoe insert of claim 5 wherein the chemical substance is ammonium nitrate.

7. The shoe insert of claim 6 wherein the chemical substance is inserted into the plurality of indentations.

8. The shoe insert of claim 6 wherein the liquid comprises water.

9. The shoe insert of claim 8 wherein the liquid further comprises a viscous liquid.

10. The shoe insert of claim 1 wherein the cushioned layer is sandwiched between the top and bottom components.

11. The shoe insert of claim 1 further comprising a plurality of break-away strips at the toe end, said strips being joined together such that individual strips can be removed from the insert, in order that the size of the insert can be adjusted to fit a range of shoe sizes by removing one or more of the break-away strips from the insert.

* * * * *